United States Patent [19]

Young, Jr. et al.

[11] Patent Number: 5,458,601
[45] Date of Patent: Oct. 17, 1995

[54] ADJUSTABLE LIGAMENT ANCHOR

[75] Inventors: Franklin A. Young, Jr., Wadmalaw Island; Yuehuei An, Charleston, both of S.C.

[73] Assignee: Medical University of South Carolina, Charleston, S.C.

[21] Appl. No.: 218,356

[22] Filed: Mar. 28, 1994

[51] Int. Cl.$^6$ ............................................. A61B 17/00
[52] U.S. Cl. ........................ 606/72; 606/73; 606/151; 606/232
[58] Field of Search ............................. 606/151, 232, 606/213, 60, 62, 63, 65, 67, 68, 72, 73; 623/1, 13

[56] References Cited

U.S. PATENT DOCUMENTS

| | | | |
|---|---|---|---|
| 2,112,007 | 3/1938 | Adams | 606/72 |
| 4,772,286 | 9/1988 | Goble et al. | |
| 4,828,562 | 5/1989 | Kenna | 623/13 |
| 4,870,957 | 10/1989 | Goble et al. | 623/13 |
| 5,084,050 | 1/1992 | Draenert | |
| 5,100,405 | 3/1992 | McLaren | 606/73 |
| 5,108,431 | 4/1992 | Mansat et al. | |
| 5,108,433 | 4/1992 | May et al. | |
| 5,116,337 | 5/1992 | Johnson | |
| 5,129,902 | 7/1992 | Goble et al. | |
| 5,151,104 | 9/1992 | Kenna | 606/73 |
| 5,152,790 | 10/1992 | Rosenberg et al. | 623/13 |

FOREIGN PATENT DOCUMENTS

| | | | |
|---|---|---|---|
| 232049 | 8/1987 | European Pat. Off. | 606/73 |
| 2688689 | 9/1993 | France | 623/13 |
| 405300917 | 11/1993 | Japan | 623/13 |
| 2078528 | 1/1982 | United Kingdom | 623/13 |

Primary Examiner—Tamara L. Graysay
Assistant Examiner—Jeffrey A. Schmidt
Attorney, Agent, or Firm—Needle & Rosenberg

[57] ABSTRACT

The invention provides an adjustable ligament anchor for attaching a ligament to a bone. The ligament anchor comprises a housing having an exterior surface, an interior surface, an intra-articular end and an opposite extra-articular end. The interior surface defines a bore that extends longitudinally through the housing, joining the ends. A member is dimensioned to be received within the bore and having a first end and an opposite second end, wherein the ligament is attached to the first end. Adjusting means comprise a longitudinal chamber opening through the second end, and extending into at least a portion of the member. The chamber has threads and is dimensioned to receive a screw having a shaft with threads complimentary to threads in chamber.

9 Claims, 1 Drawing Sheet

ADJUSTABLE LIGAMENT ANCHOR

BACKGROUND OF THE INVENTION

1. Field of the Invention

This invention relates to a ligament anchor for use in a surgical procedure and particularly relates to repair or replacement of a knee cruciate ligament.

2. Prior Art

In the prior art, many fixation devices have been invented for use in repairing joints, which have been injured. Examples of arrangements for attaching ligaments to the tibia and femur are shown in U.S. Pat. Nos. 5,152,790 (Rosenberg et al., Oct. 6, 1992); 5,151,104 (Kenna, Sep. 29, 1992); 5,129,902 (Goble et al., Jul. 14, 1992); 5,116,337 (Johnson, May 26, 1992); 5,108,433 (May et al., Apr. 28, 1992); 5,108,431 (Mansat et al., Apr. 28, 1992); 5,084,050 (Draenert, Jan. 28, 1992); 4,870,957 (Goble et al. Oct. 3, 1989); 4,828,562 (Kenna, May 9, 1989); and 4,772,286 (Goble et al., Sep. 20, 1988). None of the devices described in the prior art provide effective means for anchoring a ligament that remains fully adjustable after surgical implantation and which does not require breaking of any contact between the device and the bone in which it is implanted in order to repair or replace the ligament. Thus, despite extensive efforts made in this field, the need still exists for a ligament anchor which permits an unlimited number of retensionings and in which it is not difficult to replace a prosthetic ligament.

The present invention meets these needs by providing an adjustable ligament anchor as described herein.

SUMMARY OF THE INVENTION

The invention provides an adjustable ligament anchor for attaching a ligament to a bone. The ligament anchor comprises a housing having an exterior surface, an interior surface, an intra-articular end and an opposite extra-articular end. The interior surface defines a bore that extends longitudinally through the housing, joining the ends. Means for attaching a ligament to the housing comprise a member dimensioned to be received within the bore and having a first end and an opposite second end, wherein the ligament is attached to the first end. Adjusting means comprise a longitudinal chamber opening through the second end, and extending into at least a portion of the member. The chamber has threads and is dimensioned to receive a screw having a shaft with threads complimentary to threads in the chamber.

The present invention has the advantage of permitting adjustment of, or complete replacement of, the ligament without breaking contact between the housing and the bone. A further advantage of the present ligament anchor is that there is no need to anchor the ligament to any extra-articular bone cortex.

BRIEF DESCRIPTION OF THE DRAWINGS

FIG. I is a blown apart perspective view of the ligament anchor.

DETAILED DESCRIPTION OF THE INVENTION

Figure 2:
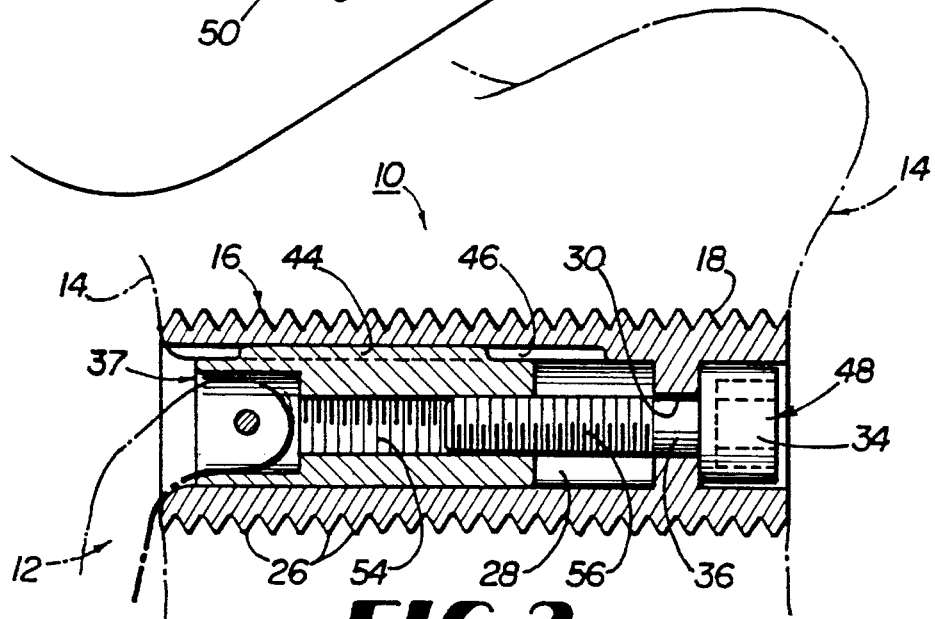
FIG. 2 is a cut-away side plan view or the ligament anchor.

The present invention is described with reference to the drawings. FIG. 2 shows the adjustable ligament anchor 10 for attaching a ligament 12 to a bone 14.

The ligament anchor 10 comprises a housing 16 having an exterior surface 18, an interior surface 20, an intra-articular end 22 and an opposite extra-articular end 24. The housing 16 can be of various shapes, although an elongated cylindrical shape is generally preferred. The material of which the housing 16 is constructed will be stainless steel, titanium or titanium alloys, cobalt chromium alloys, tantalum or tantalum alloys. Other suitable metals or metal alloys, which possess strength and corrosion resistance and are compatible with bone tissue can also be used.

The exterior surface 18 is non-uniform or textured. For example, the surface can be threaded as with exterior threads 26 (FIGS. 1 and 2), crenulated, beaded or otherwise given a texture that will enhance the adherence of bone 14 to the ligament anchor 10. A combination of threads and other texturing can be used to enhance fixation of the anchor in bone. The texturing will also impede the anchor 10 from rotating in, or being pulled out of bone 14. However, as shown in FIG. 2, it is preferred that the intra-articular end 22 be rounded and smooth, so that damage to the ligament from any potential contact with housing 16 will be minimized.

Figure 1:
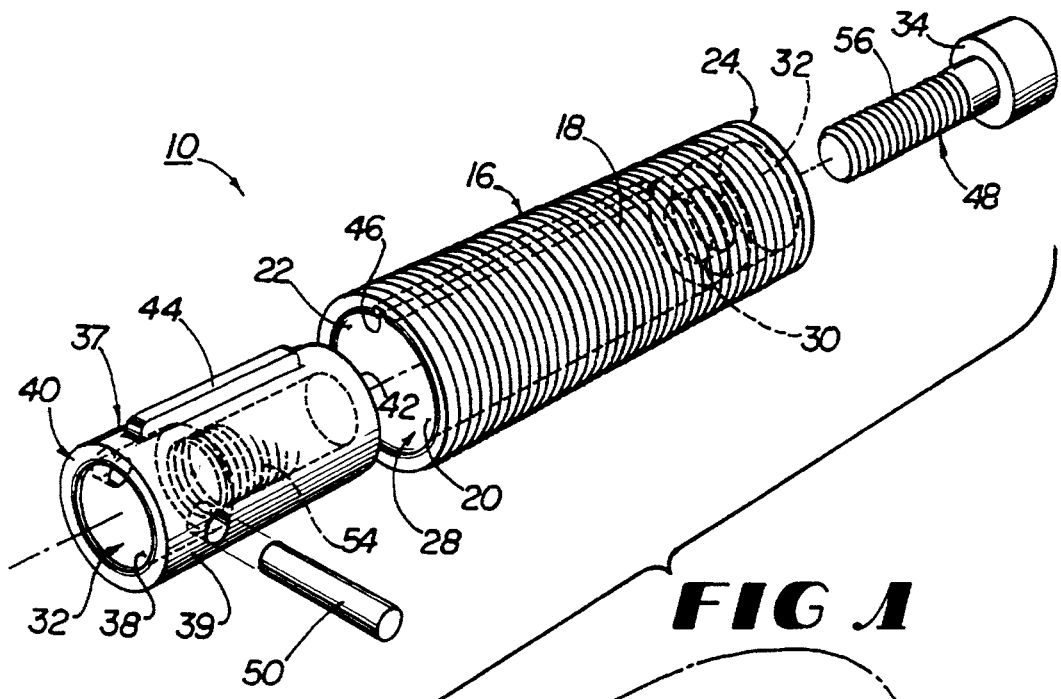

The interior surface 20 defines a bore 28 that extends longitudinally through the housing 16, joining the ends 22,24. As shown in FIG. 1, the interior surface 20 of the housing 16 can define an area of reduced diameter 30 that forms a subchamber 32 of bore 28 adjacent the extra-articular end 24. A screw (described below), used to adjust the tension on the ligament 12, fits within the bore 28 with the screw head being dimensioned to fit within subchamber 32. The interior surface 20 can also define a slot 46 extending longitudinally through at least a portion of the bore 28. As described below the slot 46 is part of a means for maintaining the position of the ligament 12 in the housing 16.

As shown in FIG. 1, the ligament anchor 10 includes a member 37 dimensioned to be received within the bore 28 and having a first end 40 and an opposite second end 42. As shown in FIGS. 1, the member 37 can have an inner surface 38 and an outer surface 39 that defines a longitudinally extending key 44 which is dimensioned to be received within the slot 46 formed in the interior surface 20 of the housing 16. By this design and others based on the same principal, member 37 is prevented from rotating about its longitudinal axis within the bore 28.

As shown in FIG. 1, member 37 also comprises a longitudinal chamber 52 opening through the second end 42, and extending into at least a portion of the member 37. The chamber 52 has chamber threads 54 and is dimensioned to receive a screw 48.

The screw 48 has a shaft 36 with screw threads 56 complimentary to chamber threads 54 in chamber 52 and a head 34 on one end of the shaft 36 formed of a portion of the screw 48 having a larger cross-sectional dimension than the shaft 36. The head 34 is on the end of shaft 36 adjacent the extra-articular end 24 of the housing 16 when the screw 48 is in place. The largest cross-sectional dimension of the head 34 is larger than the smallest cross-sectional dimension of the bore 28 (e.g., at the area of reduced diameter 30) to prevent head 34 from pulling through the bore 28. The largest cross-sectional dimension of the head 34 is smaller than the smallest cross-sectional dimension of subchamber 32 so that head 34 can fit within subchamber 32 and turn freely therein. The shaft 36 of screw 48 is dimensioned to pass through the area of reduced diameter 30 and is rotatable within the bore 28. Although described above with reference to a specific embodiment, the screw can include any suitable device having a shaft and head with the described characteristics.

Figure 3:
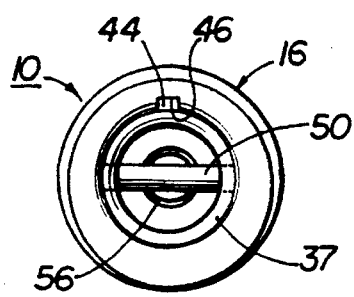
FIG. 3 is a plan view of the intra-articular end of the ligament anchor.

As shown in FIG. 2, ligament 12 can be attached to the first end 40 of member 37. The means for attaching the ligament 12 to member 37 can be chosen from among the many conventional fasteners or other means currently used in this context or later discovered to be suitable in the present use. Examples of such fastening means include pins, rivets, bolts, clevis pins (for ligaments with end loops), screws, clamps, sutures, staples, adhesives and luting. Luting is understood in the art to describe the use of a filling material that holds the ligament in place by exerting pressure on its surface. A preferred attaching means, pin 50, and its positioning on member 37 are shown in FIGS. 1 and 3.

Ligament anchor 10 includes means for adjusting the position of member 37 within the bore 28. The adjusting means, shown in FIGS. 1, 2 and 4, comprise the longitudinal chamber 52 and screw 48. By adjusting the position of member 37 within bore 28, the tension on ligament 12, attached to member 37, can be adjusted.

Figure 4:
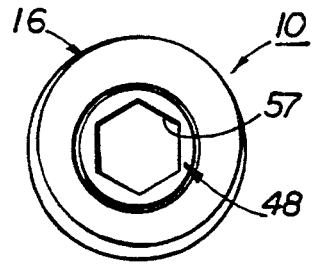
FIG. 4 is a plan view of the extra-articular end of the ligament anchor.

Adjustment of the ligament can be accomplished by turning the screw 48 by its head 34 for example, with a screw driving tool. FIG. 4 shows head 34 with a hex socket recess 57 that can be turned by a hex wrench. By turning head 34, shaft 36 rotates and screw threads 56 engage chamber threads 54, causing the member 37 to move longitudinally within the bore 28. The member 37 moves longitudinally, because its rotational movement is impeded by the interaction of means such as key 44 and slot 46. When a ligament 12 is attached to the member 37, the longitudinal movement of a member 37 increases tension on the ligament if member 37 moves toward the extra-articular end 24 of the housing 16. Tension on the ligament is reduced if member 37 moves toward the intra-articular end 22 of the housing 16. The movement of the member 37 toward the extra-articular end of housing 16 is ultimately limited by interior surface 20 in the area of reduced diameter 30 in bore 28, because the diameter of member 37 is larger than the diameter of the bore 28 in the area of reduced diameter 30.

The tension on a ligament anchored by the present ligament anchor 10 can be adjusted by accessing screw head 34 in subchamber 32 at the extra-articular 24 end of housing 16. Using the present invention there is no need for arthrotomy or arthroscopy in order to adjust the tension of the ligament.

The present invention also has the advantage of permitting complete replacement of the ligament 12 without removing the housing 16 from the bone 14. When the anchor 10 is used in both of the bones being joined, the screws 48 can be disengaged from both members 37 and the members 37 with the ligament 12 attached can be removed from the joint by pulling the members 37 out of their respective housings 16. A new ligament 12 can be installed by reversing the process described above. Ligament replacement can be done without open reduction of the joint. The incisions will be slightly larger than for conventional arthroscopy.

The adjustable ligament anchors, according to the present invention, can be positioned in the knee joint, preferably in the following manner. First, a small diameter tunnel is drilled through the tibial and femoral portions of the knee joint bones in any suitable manner. The tunnel must be large enough to accommodate the housing. If a partially or totally threaded implant housing 16 is employed, the bone is tapped to the proper thread and the housing 16 is screwed into place using an appropriate holding tool. For other methods of fixation, the tunnel in the bone is drilled to a size such that the implant can be tapped into place with a slightly interfering fit. The housing 16 is then further secured to bone 14 by bone growth into exterior threads 26 or other textured areas of housing 16. These and other methods are well known and routinely practiced by an orthopedic surgeon.

The housing, if necessary, can be cut from the bone interface with a core drill and relatively easily removed. However, a significant advantage of the present ligament anchor is that there is generally no need to remove the ligament anchor for either ligament tension adjustment or replacement.

While the invention has been described in detail with particular reference to the preferred embodiment thereof, it will be understood that variations and modifications can be effected within the spirit and scope of the invention as previously described and as defined by the claims.

What is claimed is:

1. An adjustable ligament anchor for attaching a ligament to a bone using a ligament attaching means, comprising:

(a) a housing having an exterior surface, an intra-articular end and an opposite extra-articular end and an interior surface defining a bore extending longitudinally through the housing, joining the ends;

(b) a member dimensioned to be received within the bore and having a first end and an opposite second end;

(c) a longitudinal chamber opening through the second end, and extending into a portion of the member, wherein the chamber is threaded;

(d) a screw having a shaft with threads thereon being complimentary to the threads in the chamber, and having a head on one end of the shaft adjacent the extra-articular end of the housing, the head being formed of a portion of the shaft having a larger cross-sectional dimension than the shaft adjacent the head, wherein the largest cross-sectional dimension of the head is larger than the smallest cross-sectional dimension of the bore; and (e) means on the first end of the member for receiving the ligament attaching means.

2. The anchor of claim 1, wherein the exterior surface is non-uniform.

3. The anchor of claim 2, wherein the exterior surface is crenulated.

4. The anchor of claim 2, wherein the exterior surface is threaded.

5. The anchor of claim 2, wherein the exterior surface is beaded.

6. The anchor of claim 1, wherein the surface defining the bore defines a slot extending through at least a portion of the bore, and wherein the member has an exterior surface defining a longitudinally extending key dimensioned to be received within the slot, whereby the member is prevented from rotating about its longitudinal axis within the bore.

7. The anchor of claim 1, wherein the surface defining the bore defines an area of reduced diameter, forming a subchamber adjacent the extra-articular end, and wherein the shaft is dimensioned to pass through the area of reduced diameter and is rotatable within the bore.

8. The anchor of claim 7, wherein the largest cross-sectional dimension of the head is larger than the largest cross-sectional dimension of the bore in the area of reduced diameter.

9. The anchor of claim 8, wherein the largest cross-sectional dimension of the head is smaller than the smallest cross-sectional dimension of the subchamber.

* * * * *